(12) United States Patent
Senft

(10) Patent No.: US 8,390,037 B2
(45) Date of Patent: Mar. 5, 2013

(54) GAS SENSOR

(75) Inventor: Christoph Senft, Munich (DE)

(73) Assignee: Micronas GmbH, Freiburg I.BR. (DE)

( * ) Notice: Subject to any disclaimer, the term of this patent is extended or adjusted under 35 U.S.C. 154(b) by 0 days.

(21) Appl. No.: 12/983,866

(22) Filed: Jan. 3, 2011

(65) Prior Publication Data
US 2011/0163353 A1   Jul. 7, 2011

Related U.S. Application Data

(63) Continuation of application No. PCT/EP2009/004577, filed on Jun. 25, 2009.

(30) Foreign Application Priority Data

Jul. 2, 2008   (EP) .................................... 08011919

(51) Int. Cl.
*G01N 27/403* (2006.01)
(52) U.S. Cl. ................................ 257/253; 257/E29.242
(58) Field of Classification Search .................. 257/253, 257/E29.242
See application file for complete search history.

(56) References Cited

U.S. PATENT DOCUMENTS

| 7,495,300 | B2 * | 2/2009 | Gardner et al. ................ 257/414 |
| 2002/0131898 | A1 | 9/2002 | Fleischer et al. | |

FOREIGN PATENT DOCUMENTS

| DE | 40 28 062 A1 | 3/1992 |
| DE | 43 33 875 A1 | 4/1995 |
| EP | 1104884 A2 | 6/2001 |
| JP | 2-268265 A | 11/1990 |
| JP | 7-146272 A | 6/1995 |
| JP | 2003-066042 A | 3/2003 |
| JP | 2006-084417 A | 3/2006 |

OTHER PUBLICATIONS

Senft C. et al: "Cross Sensitivity and Stability of FET—Based Hydrogen Sensors", Sensors, 2007 IEEE, IEEE, PI, Oct. 28, 2007, pp. 1036-1039; XP031221242; ISBN: 978-1-4244-1261-7; abstract, figures 1, 3.

Sato T. et al: "Light-addressable suspended-gate gas sensor"; Sensors and Actuaors B, Elsevier Sequoia S.A., Lausanne, CH, vol. B20, No. 2/03, Jun. 1, 1994, pp. 213-216, XP000478162; ISSN: 0925-4005; abstract; figure 2.

Scharnagl K et al: "Hydrogen detection at high concentrations with stabilised palladium", Sensors and Actuators B, Elsevier Sequoia S.A., Lausanne, CH, vol. 78, No. 1-3, Aug. 30, 2001, pp. 138-143, XP004297648, ISSN: 0925-4005; abstract; figure 7.

* cited by examiner

*Primary Examiner* — Kimberly Rizkallah
*Assistant Examiner* — Timor Karimy
(74) *Attorney, Agent, or Firm* — Muncy, Geissler Olds & Lowe, PLLC

(57) ABSTRACT

A gas sensor having at least one gas-sensitive electrically conductive layer having a surface region which can be brought into contact with a target gas and in which the work function depends on the concentration of the target gas in contact therewith. At least one electrical potential sensor is capacitively coupled to the surface region via an air gap. The surface region is structured by at least one recess in which a flat material element which is connected to the gas-sensitive layer in an electrically conductive manner is arranged, the material of the material element differing from that of the gas-sensitive layer and comprising a metal and/or a metal-containing chemical compound.

21 Claims, 9 Drawing Sheets

GAS SENSOR

This nonprovisional application is a continuation of International Application No. PCT/EP2009/004577, which was filed on Jun. 25, 2009, and which claims priority to European Patent Application No. EP 08011919.1, which was filed on Jul. 2, 2008, and which are both herein incorporated by reference.

BACKGROUND OF THE INVENTION

1. Field of the Invention

The present invention relates to a gas sensor with at least one gas-sensitive, electrically conductive layer, having a surface region which can be brought into contact with a target gas and in which the work function depends on the concentration of the target gas in contact therewith, and with at least one electric potential sensor capacitively coupled to the surface region via an air gap.

2. Description of the Background Art

A gas sensor for measuring the hydrogen gas concentration is disclosed in DE 43 33 875 C2. The gas sensor has a silicon substrate, in which as a potential sensor a field-effect transistor with a drain, a source, and a channel region located between these is integrated. An electrical insulation layer is arranged on the channel region and a gate electrode thereupon. To the side of the gate electrode, a sensor electrode is provided, which is connected integrally to the gate electrode to form a suspended gate. On its lower side facing the substrate, the sensor electrode is coated with a gas-sensitive layer, which is capacitively coupled to the source via the air gap. A surface region, facing the substrate, of the gas-sensitive layer can be brought into contact with the hydrogen gas, which during the contacting of the surface region is adsorbed on said region. With a change in the hydrogen gas concentration, the work function changes in the surface region of the gas-sensitive layer. Because the sensor electrode is capacitively coupled to the surface region and connected to the gate electrode, the electric potential at the gate electrode also changes thereby. The current flow between the drain and source is controlled depending on the change in potential.

In normal indoor air, a thin layer of atmospheric oxygen is adsorbed dissociatively on the surface of the gas-sensitive layer, i.e., as oxygen atoms, not as oxygen molecules as they occur in air. When the target gas enters the vicinity of the gas-sensitive layer, an adsorption of the target gas on the surface occurs first, whereby the target gas partially displaces the atmospheric oxygen adsorbed on the surface and occupies its adsorption sites. Both effects, the adsorption of the target gas and reduction of the oxygen occupancy, contribute additively to the change in the surface work function. At the same time, however, a reaction between hydrogen and oxygen, during which water is formed, occurs on the surface, promoted by the catalytic action of the gas-sensitive layer. As a result, at low temperatures below about 60° C., only the hydrogen coverage on the surface is reduced gradually. This hydrogen consumption is compensated by continuous new adsorption of hydrogen from the gas phase, so that a stable measuring signal is assured. At higher temperatures above about 60° C., the reaction proceeds so rapidly that the hydrogen adsorption can no longer fully compensate for the hydrogen consumption by the surface reaction and, additionally, also the hydrogen concentration in the immediate vicinity of the gas-sensitive layer is reduced. The oxygen coverage of the surface can again increase as a result. All three effects shift the work function in the opposite direction. This reaction can occur within hours or also within seconds, depending on the temperature of the gas-sensitive layer, so that the measuring signal can be greatly disrupted.

SUMMARY OF THE INVENTION

It is therefore an object of the present invention to provide a gas sensor of the aforementioned type, which enables a high measuring accuracy.

This object is achieved in that the surface region is structured by at least one recess, in which a flat material element is arranged, which is connected to the gas-sensitive layer in an electrically conductive manner and whose material differs from that of the gas-sensitive layer and comprises at least one metal and/or at least one metal-containing chemical compound.

Surprisingly, it turned out that the gas-sensitive layer is stabilized by this structuring so far that the interaction of the reactions of the target gas to be measured can be reduced or even stopped with the surface and atmospheric oxygen. The chemical compound is preferably an oxide. The gas-sensitive layer consists preferably of metal, particularly of platinum and/or palladium.

Tests have shown that the measuring signal of the gas sensor is stabilized especially well when the at least one metal comprises silver and/or copper.

It is advantageous when the structure formed by the surface region and the at least one material element is produced with a masking step, especially by photolithography. It is possible thereby to produce the structure during the fabrication of the gas sensor selectively and reproducibly with a predefined geometry. The structure is preferably designed in a regular manner and/or has regular basic geometric forms. In the view looking at the gas-sensitive layer, the structure may have straight, curved, square, rectangular, polyangular, polygonal, elliptical, and/or ring-shaped structural elements. A set, which has at least two of the gas sensors of the invention, in which the structures are identical or match, is also within the scope of the invention.

The at least one metal, however, may also comprise iron, tin, lead, nickel, zinc, and/or cobalt. These metals are next to silver and copper in the electrochemical series.

In an embodiment of the invention, the surface region, which can be brought into contact with the target gas of the gas-sensitive layer, is greater than 1%, optionally greater than 5%, and especially greater than 10% of the surface, which can be brought into contact with the target gas, of the at least one material element located within the at least one recess. A too small surface region, which can be brought into contact with the target gas, of the gas-sensitive layer on the surface leads to a low target gas adsorption, which however is critical for target gas detection.

It is advantageous when the surface, which can be brought into contact with the target gas, of the at least one material element, located within the at least one recess, is greater than 0.001%, optionally greater than 0.1%, and especially greater than 10% of the surface region (9), which can be brought into contact with the target gas, of the gas-sensitive layer. If the material element surface region, which can be brought into contact with the target gas, is too small, the stabilizing effect of the at least one material element declines.

The surface region, which can be brought into contact with a target gas, can be structured such that the surface region is not more than 500 µm at any place, optionally more than 300 µm, and especially more than 100 µm away from the at least one material element. An effective stabilization of the measuring signal of the gas sensor is made possible as a result.

The structure formed by the surface region and the at least one material element can have at least two matching unit structure regions, which are preferably adjacent laterally and each comprise at least one material element and a section of the surface region of the gas-sensitive layer. In this case, it is even possible that the structure is formed by a plurality of such unit structure regions, which are arranged side-by-side in one or more rows in the form of a matrix.

It is advantageous when at least two of the material elements are spaced apart laterally from one another by a subregion, located between the elements, of the gas-sensitive layer and when the distance of the material elements is at least 50 nm, optionally at least 75 nm, and preferably at least 100 nm. In this case, it is even possible that the material elements are separated from one another in that they are enclosed completely, for example, by the gas-sensitive layer. The material element outer contour, adjacent to the gas-sensitive layer, is preferably selected so that the boundary, along which the material elements border the gas-sensitive layer, is as short as possible. This can be achieved particularly by designing the material elements in the form of a circular disk.

In an embodiment of the invention, the thickness of the flat material elements can be at least 0.1 times the thickness of a monolayer and at most 10 μm. Tests have shown that good stabilization of the measuring signal can be achieved with a layer thickness of 10 nm with a flat material element made of copper or copper oxide.

In another embodiment of the invention, the at least one material element can be arranged on the gas-sensitive layer. The converse arrangement is also possible, however, in which the gas-sensitive layer is arranged on a metal layer, whereby at least one subregion, not covered by the gas-sensitive layer, of the metal layer forms the at least one material element. In the production of the gas sensor, then only one of the two layers lying on top of one another needs to be structured. An embedded structure is also possible, however, in which the at least one material element is arranged completely in the at least one recess of the gas-sensitive layer. In the view looking at the gas-sensitive layer, the at least one material element can be arranged in front of, within, and/or behind the recess. One could also say that the at least one material element is arranged above, below, and/or in the recess.

It is advantageous when an adhesive agent layer is arranged between the at least one material element and the gas-sensitive layer. As a result, better adhesion of the at least one material element to the gas-sensitive layer can be achieved. The adhesive agent layer is preferably structured in such a way that it does not cover the gas-sensitive layer in the recesses.

It should also be mentioned that the material of the at least one material element should have long-term stability during gas exposure, preferably at temperatures to about 180° C. Particularly when the target gas is hydrogen, the at least one material element should also be resistant to moisture. Further, the at least one material element may not suppress the change in the work function of the gas-sensitive layer during contact with the target gas.

In an embodiment of the invention, the potential sensor is a field-effect transistor, which has a substrate on which a drain and a source are arranged, whereby a channel region is formed between the drain and source, whereby the channel region is capacitively coupled to the surface region of the gas-sensitive layer directly via the air gap or indirectly via a gate electrode working together with the channel region and a sensor electrode conductively connected to the gate electrode. The gas sensor can therefore have an SGFET and/or a CCFET as a potential sensor.

In another embodiment of the invention, the gas sensor is embodied as a Kelvin probe in which the potential sensor is capacitively coupled to the surface region of the gas-sensitive layer via an electrode separated by the air gap from the surface region of the gas-sensitive layer and movable toward and away from the gas-sensitive layer. A Kelvin probe of this type is used preferably in laboratory tests.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

DETAILED DESCRIPTION

Figure 1:
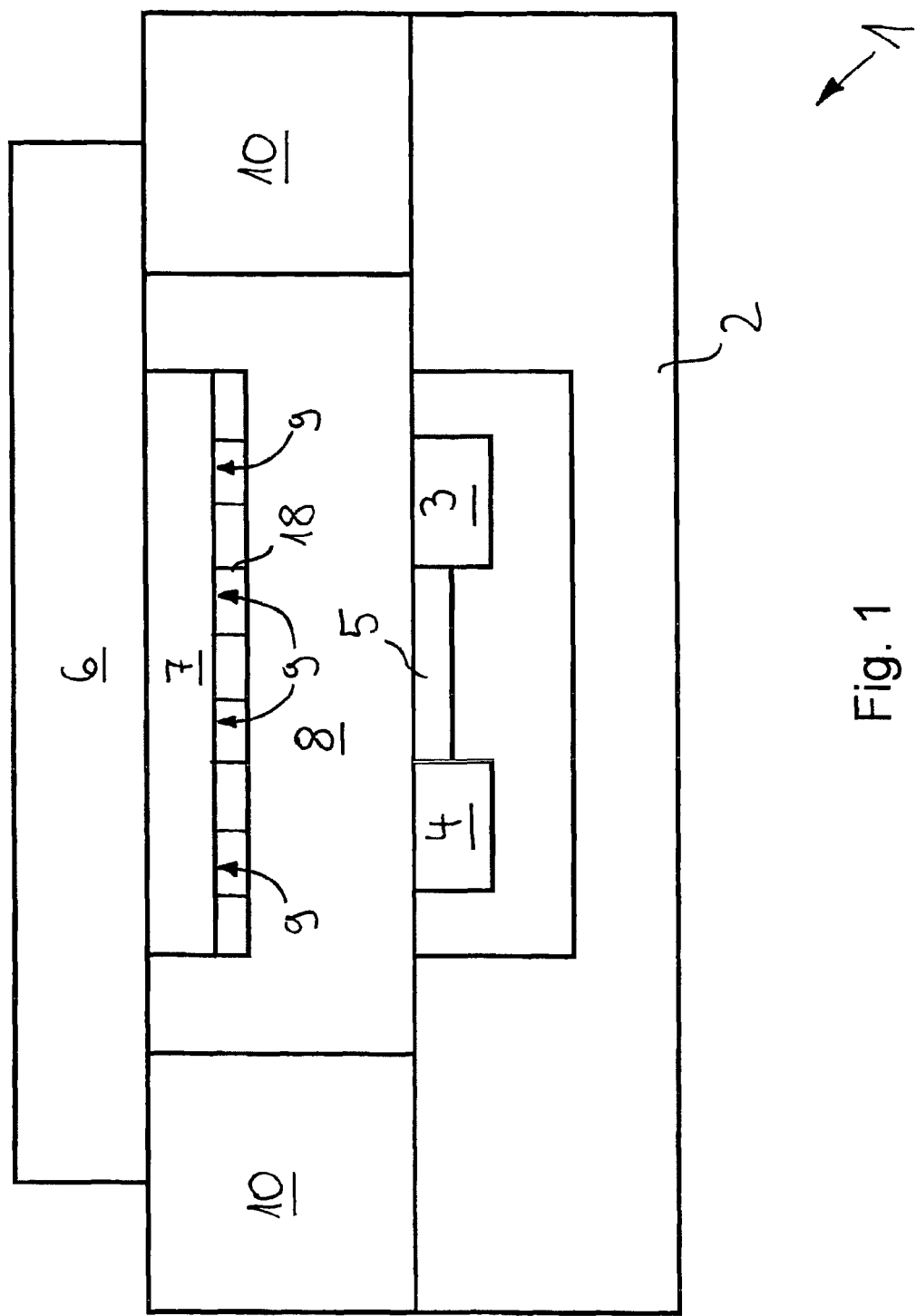
FIG. 1 shows a cross section through a gas sensor, which has an SGFET whose channel region is capacitively coupled to a gas-sensitive layer via an air gap.

A gas sensor designated as a whole by the number 1 in FIG. 1 has a substrate 2, on which a drain 3 and a source 4 are arranged in an n-doped transistor well. Drain 3 and source 4 can consist, for example, of p-doped silicon. Drain 3 is connected via electrical traces to a drain terminal, not shown in greater detail in the drawing. Source 4 is connected in a corresponding manner to a source terminal. A channel region 5, on which an electrically insulating thin oxide layer or a nitride is arranged which serves as the gate dielectric, is formed between drain 3 and source 4 in substrate 2.

A gas-sensitive layer 7, which, for example, consists of a precious metal, particularly of platinum or palladium, and is spaced apart from channel region 5 by an air gap 8, is arranged over channel region 5 on carrier part 6. A surface region 9, facing channel region 5, of gas-sensitive layer 7 is capacitively coupled via air gap 8 to channel region 5.

Carrier part 6 is connected, on both sides of gas-sensitive layer 7, to substrate 2 via an electrical insulation layer 10 in such a way that carrier part 6 and gas-sensitive layer 7 form a suspended gate.

Air gap 8 is connected via at least one opening, not shown in greater detail in the drawing, to the atmosphere surrounding gas sensor 1. Surface region 9 of gas-sensitive layer 7 can be brought into contact via this opening with a target gas to be detected, namely hydrogen. During contact with surface region 9, the target gas is adsorbed on surface region 9. In so doing, the work function in surface region 9 changes, which leads to a change in the electric potential in channel region 5.

In the exemplary embodiment according to FIG. 1, channel region 5 is formed open (ISFET) and capacitively coupled directly to gas-sensitive layer 7 via the thin layer oxide and air gap 8. It is clearly evident that channel region 5 is arranged on the side of air gap 8, said side lying opposite gas-sensitive layer 7.

Figure 2:
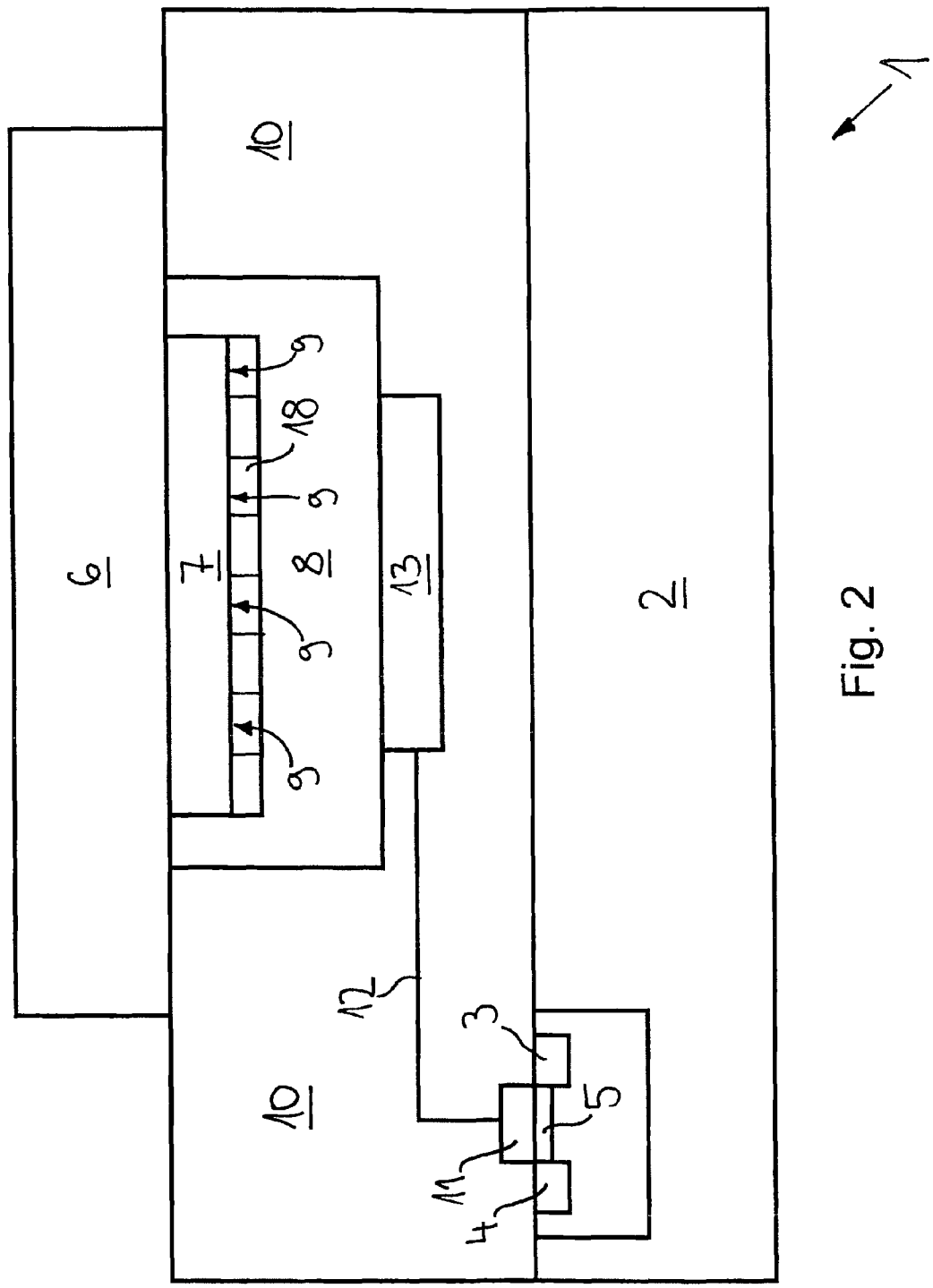
FIG. 2 shows a cross section through a gas sensor, which has a CCFET whose sensor electrode is capacitively coupled to a gas-sensitive layer via an air gap.

In the exemplary embodiment according to FIG. 2, the field-effect transistor is embodied as CCFET, in which channel region 5 is arranged laterally next to gas-sensitive layer 7 in substrate 2 and covered with a gate electrode 11. For the capacitive coupling of channel region 5 to gas-sensitive layer 7, gate electrode 11 is connected via an electric connecting line 12 to a sensor electrode 13, which is arranged on the side of air gap 8, said side opposite surface region 9 of gas-sensitive layer 7, on insulation layer 10 located on substrate 2. Insulation layer 10 can be, for example, an $SiO_2$ layer. The structure of the suspended gate of the SGFET corresponds to that in FIG. 1.

Figure 3:
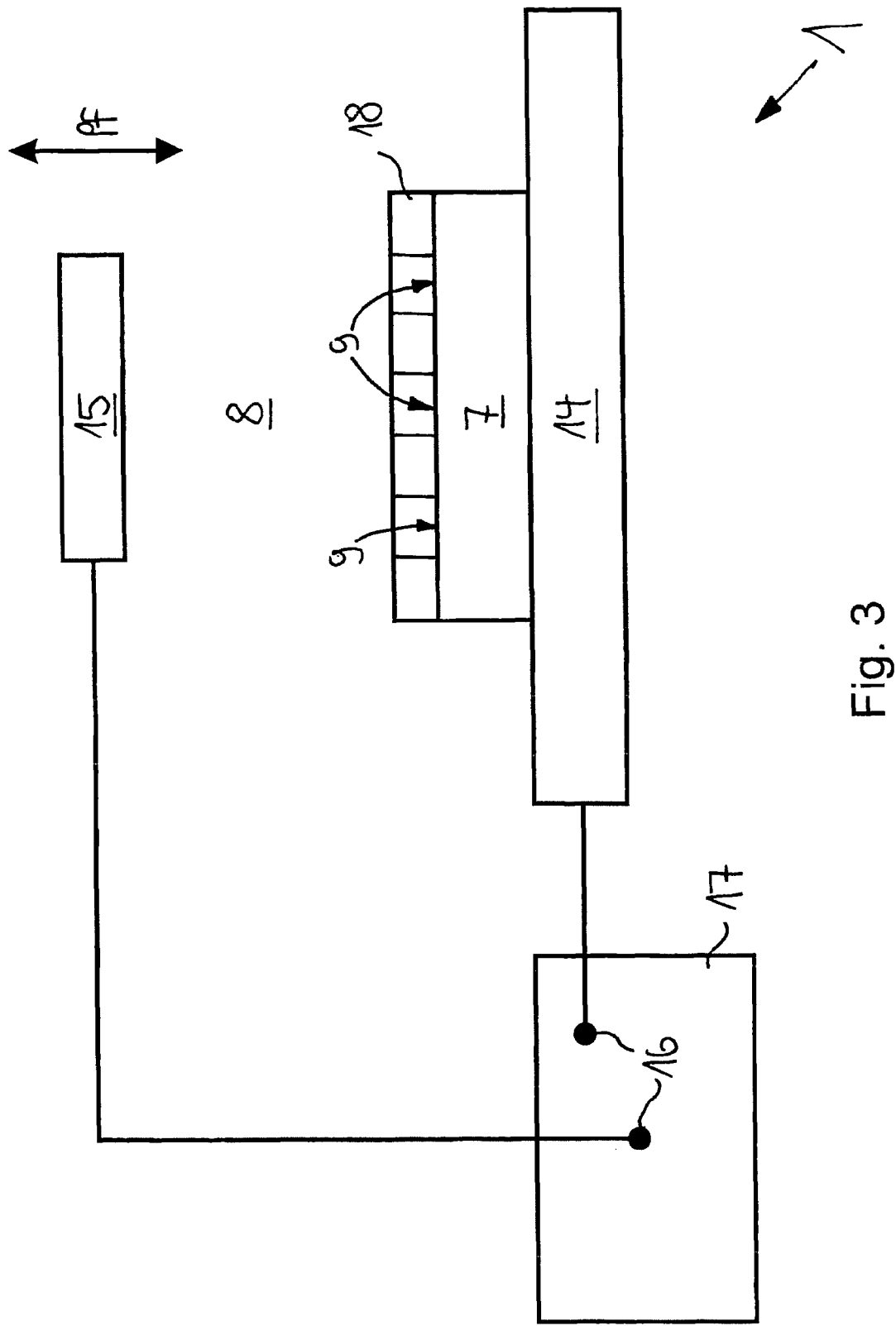
FIG. 3 shows a cross section through a gas sensor embodied as a Kelvin probe.

In the exemplary embodiment shown in FIG. 3, gas sensor 1 is embodied as a Kelvin probe. Gas-sensitive layer 7 is arranged on an electrically conductive carrier 14 and has on its side facing away from carrier 14 a surface region 9, on which the target gas can be adsorbed. Surface region 9 is spaced apart from an electrode 15 by an air gap 8 and together with said electrode forms an electrical capacitance.

Electrode 15 can be caused to oscillate with the aid of an actuator not shown in greater detail in the drawing. In this case, electrode 15 moves alternately according to arrow Pf toward and away from gas-sensitive layer 7. Electrode 15 and carrier 14 or gas-sensitive layer 7 are connected to terminals 16 of an evaluation and control unit 17. Said unit has a potential sensor, which is not shown in greater detail in the drawing and is connected to terminals 16 for measuring the electric voltage between gas-sensitive layer 7 and electrode 15. Evaluation and control unit 17 in addition has an adjustable voltage source with a control connection to the potential sensor by means of which a counter voltage is applied between the potential sensor and electrode 15 and/or carrier 14. The counter voltage is selected so that the potential measured by the potential sensor is equal to zero on average. Alternatively, the change, caused by the oscillation, in the electrical capacitance between electrode 15 and carrier 14 can also be measured directly, for example, by measuring the electric current flowing between electrode 15 and carrier 14.

Surface region 9 of gas-sensitive layer 7 in each of the exemplary embodiments shown in FIGS. 1-3 is structured in each case by recesses by photolithography, in which in each case a flat material element 18 is arranged connected in an electrically conductive manner to the gas-sensitive layer. The material of material elements 18 differs from that of gas-sensitive layer 7 and preferably contains copper and/or silver.

The surface of gas-sensitive layer 7, said surface which is capacitively coupled to channel region 5 and can be brought into contact with the target gas, is greater than 1% and smaller than 99.999% of the total surface, consisting of the surface of the gas-sensitive layer and that of material elements 18.

Surface region 9, which can be brought into contact with the target gas, of gas-sensitive layer 7 is structured so that surface region 9 is not in any place more than 500 µm away from a material element 18.

Figure 4:
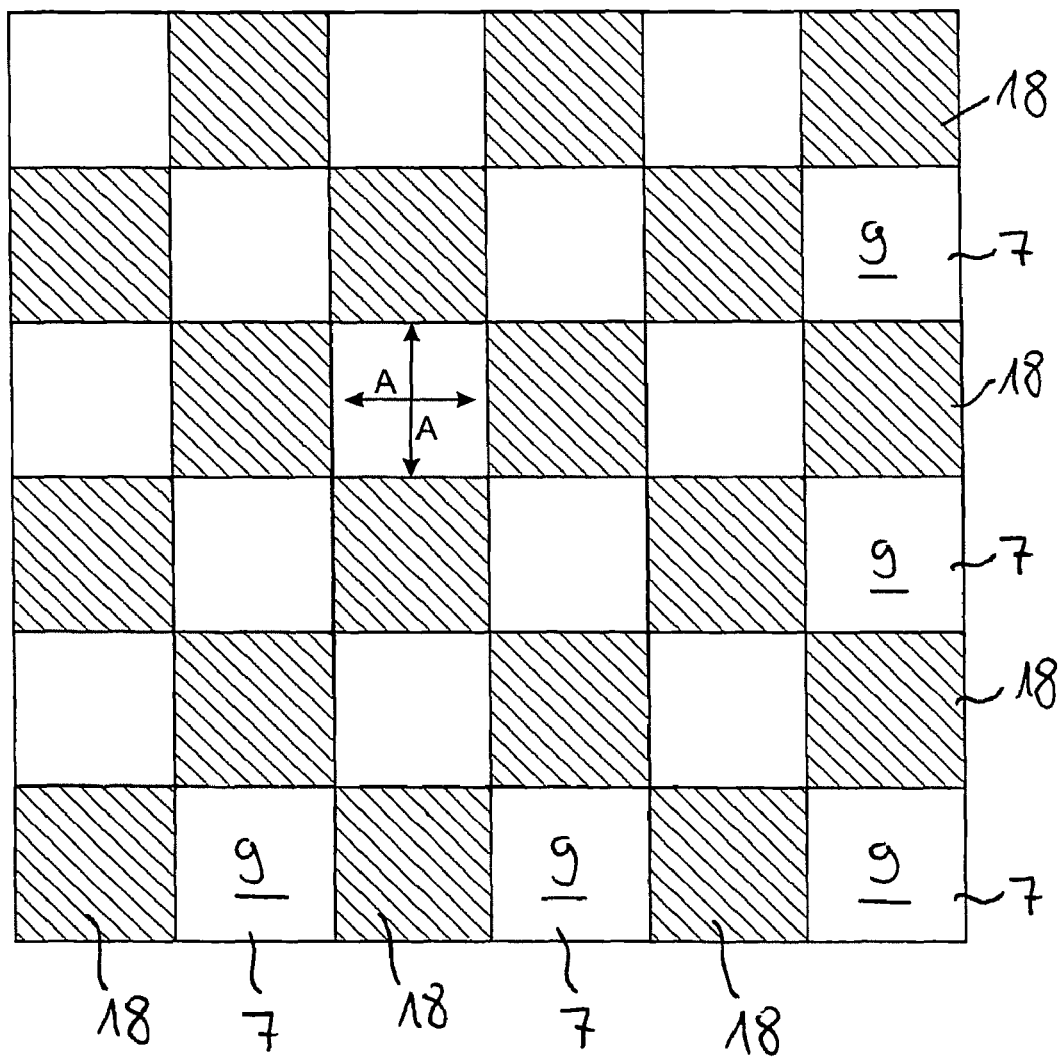
FIG. 4 shows a view of a first exemplary embodiment of a gas-sensitive layer structured by recesses.

In the exemplary embodiment shown in FIG. 4, gas-sensitive layer 7 is structured like a checkerboard. It is clearly evident that surface region 9, which can be brought into contact with the target gas, of gas-sensitive layer 7 is divided into a plurality of square sections, which are staggered in several rows and columns with gaps to one another. In the spaces between two adjacent sections of gas-sensitive layer 7, in each case a material element 18 is arranged, whose surface dimensions correspond to those of the sections. The distance A of two adjacent material elements 18 is between 100 nm and 500 µm. The area ratio of the total surface of material elements 18 to the surface region 9 of gas-sensitive layer 7 is 1:1.

Figure 5:
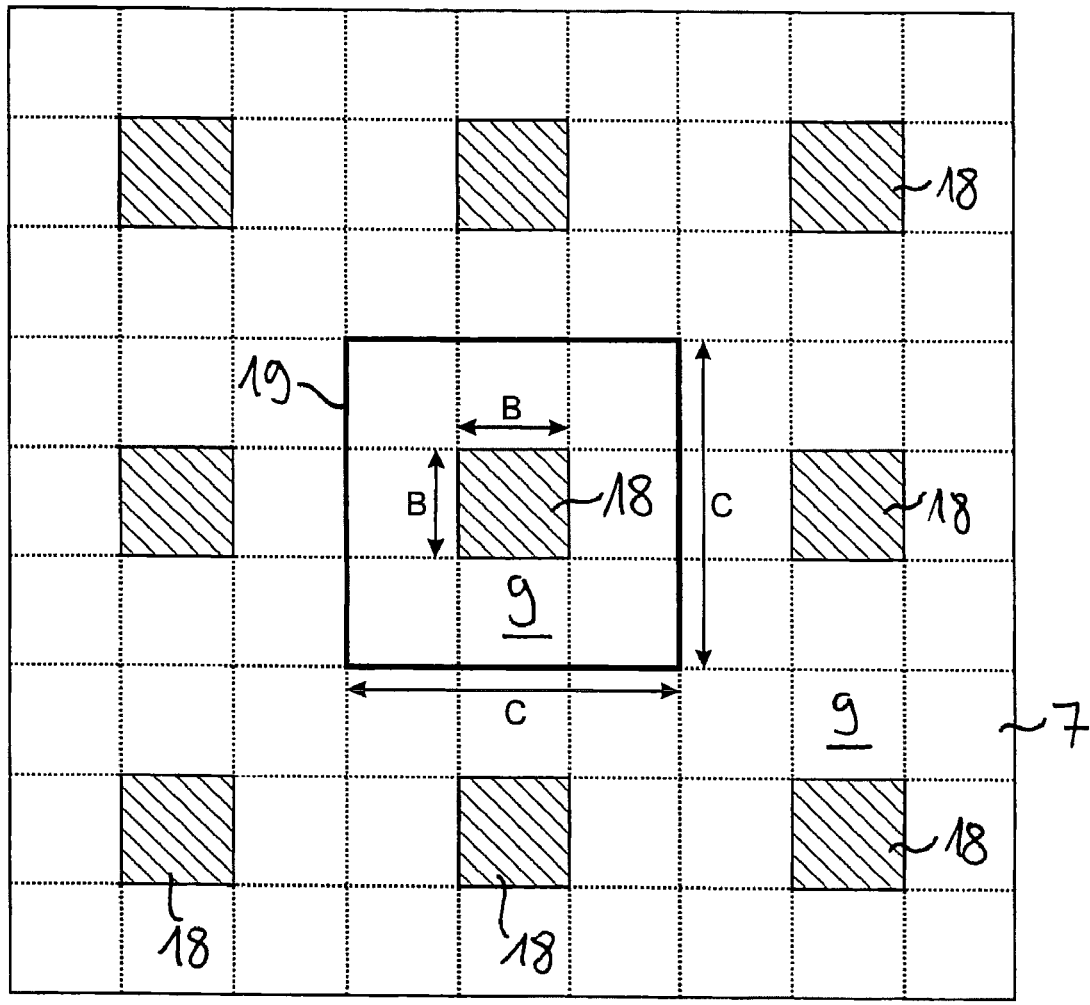
FIG. 5 shows a view of a second exemplary embodiment of a gas-sensitive layer structured by recesses.

In the exemplary embodiment shown in FIG. 5, material elements 18 are spaced apart on all sides by surface region 9, located between the sides and capable of being brought into contact with the target gas, of gas-sensitive layer 7.

It is clearly evident that the structure formed by surface region 9 and material elements 18 has several corresponding unit structure regions 19 with an approximately square outer contour. Each unit structure region 19 comprises in each case a material element 18 and a section of surface region 9 of gas-sensitive layer 7, which bounds material element 18 like a frame. Adjacent unit structure regions 19 abut sections of surface regions 9 directly and without interruptions, so that a continuous surface region 9 results which can be brought into contact with the target gas. The area ratio of the total surface of material elements 18 to surface region 9 of gas-sensitive layer 7 is $B^2/(C^2-B^2)$, where B is the edge length of material elements 18 and C the edge length of unit structure regions 19.

Figure 6:
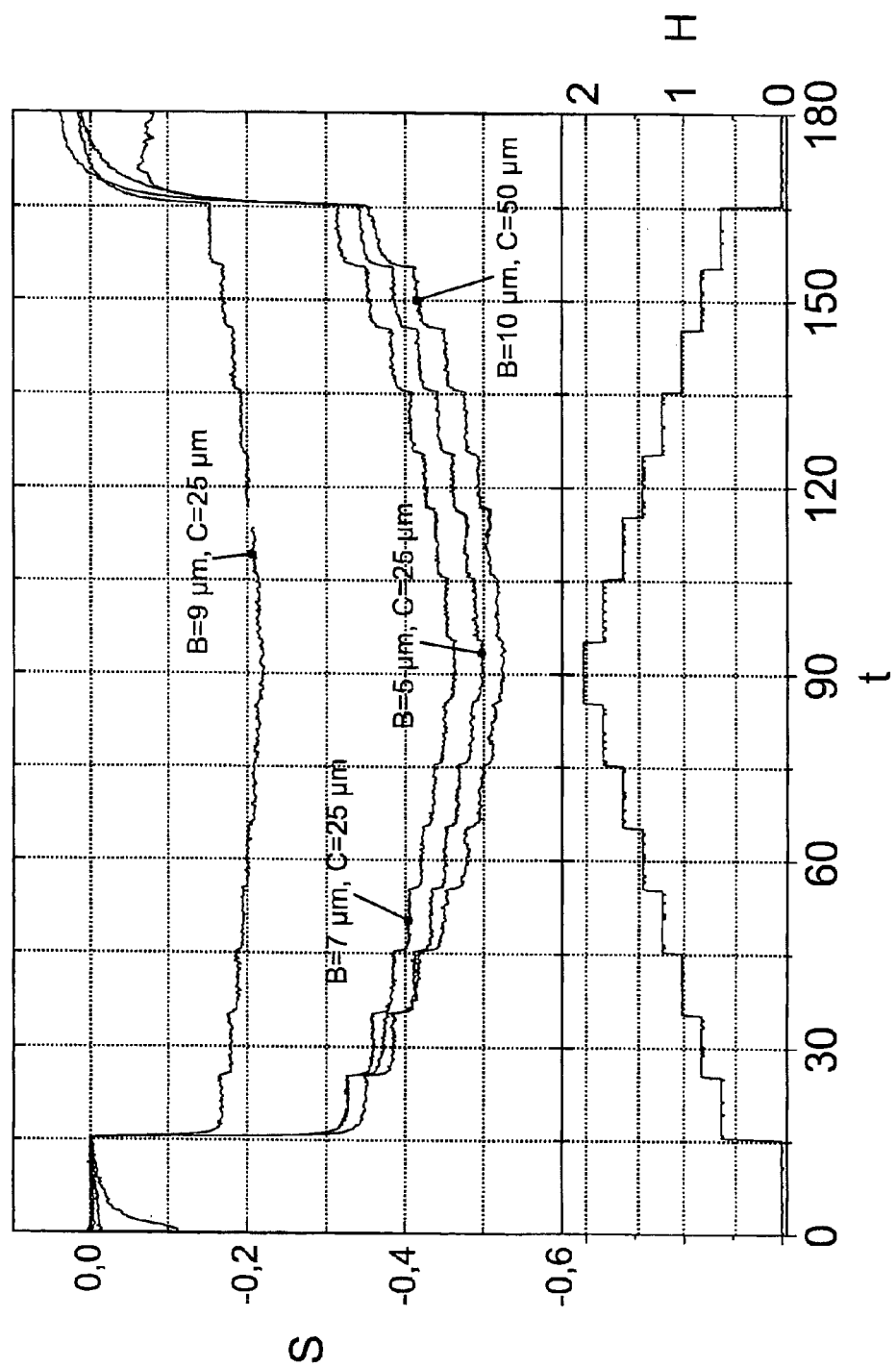
FIG. 6 is a graph of the measuring signal of a hydrogen gas sensor and the hydrogen concentration in the vicinity of the gas sensor, whereby the time t is plotted in seconds on the abscissa and the amplitude of the measuring signal is plotted on the ordinate on the left and the hydrogen concentration on the right.

The measuring signal of a Kelvin probe for different dimensions B, C (see FIG. 5) of the structure of gas-sensitive layer 7 is shown as a graph in FIG. 6, where the concentration of the target gas is increased stepwise from about zero to a maximum value and then reduced stepwise to approximately zero. It is clearly evident that the amplitude of the measuring signal depends on the dimensions of the structure and that the greatest sensitivity is achieved with the values B=10 µm and C=50 µm.

Figure 7:
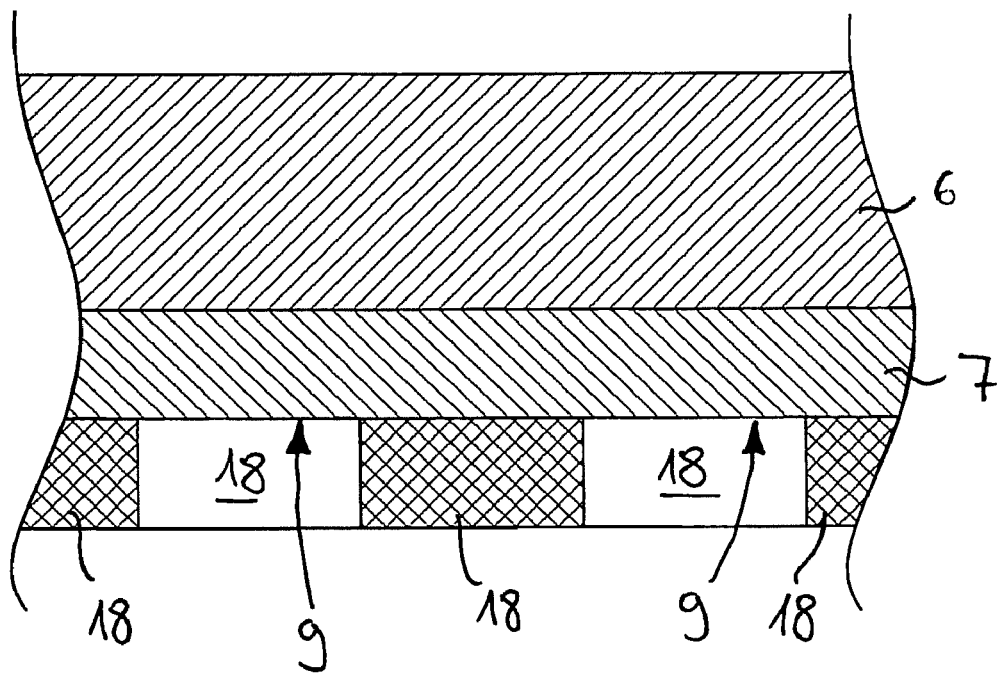
FIGS. 7 through 9 show partial cross sections through a carrier part on which a structured gas-sensitive layer is arranged.

It is evident in FIG. 7 that gas-sensitive layer 7 is arranged on carrier part 6 and material elements 18 on gas-sensitive layer 7. Gas-sensitive layer 7 runs without interruption on carrier part 6. Gas-sensitive layer 7 adheres to carrier part 6 and material elements 18 adhere to gas-sensitive layer 7. The thickness of material elements 18 is between 0.1 times the thickness of a monolayer and 10 µm. If necessary, an adhesive agent layer can be arranged between carrier part 6 and gas-sensitive layer 7 and/or between said layer and material elements 18.

Figure 8:
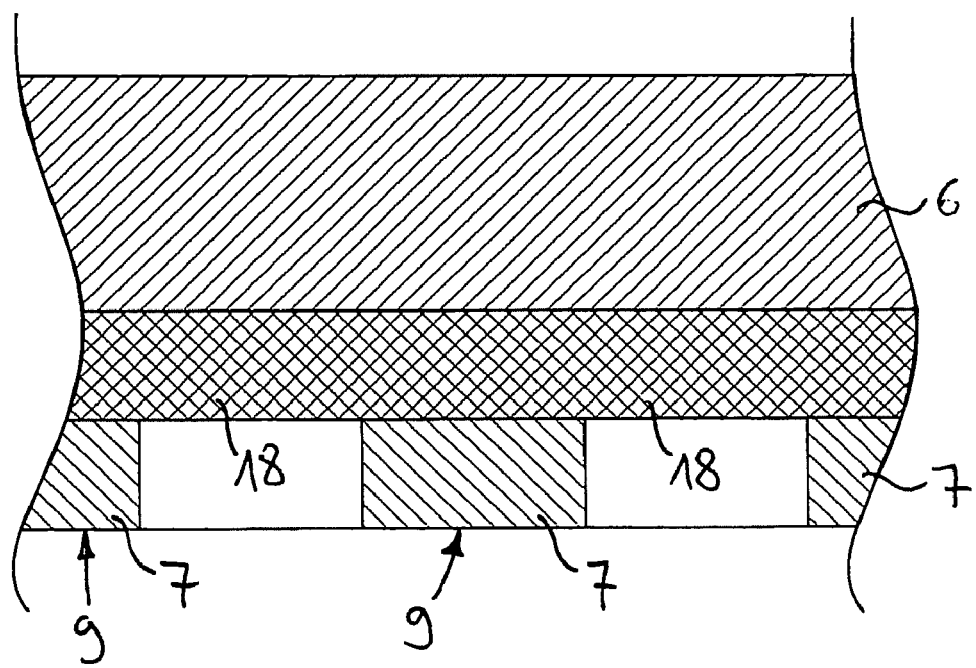

It is also possible, however, that material elements 18 are arranged on carrier part 6 and gas-sensitive layer 7 on a metal layer having material elements 18, as is shown in FIG. 8. Material elements 18 are thereby formed by sections of a continuous metal layer. The metal layer adheres to carrier part 6 and gas-sensitive layer 7 to the metal layer. If necessary, an adhesive agent layer can be arranged between carrier part 6 and the metal layer and/or between the metal layer and gas-sensitive layer 7.

Figure 9:
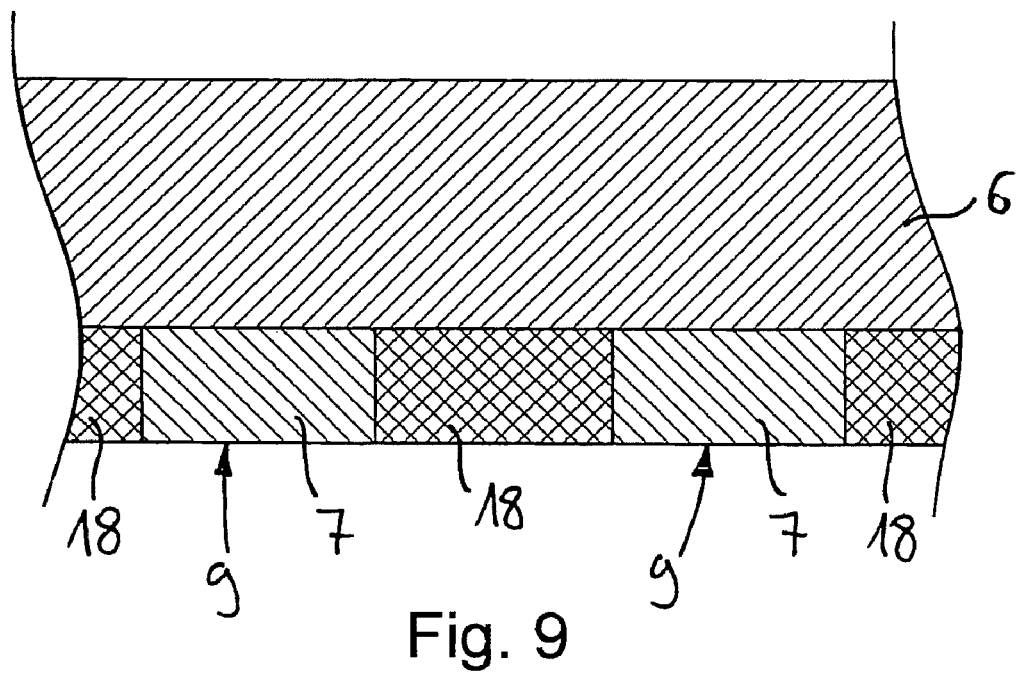

It is evident in FIG. 9 that gas-sensitive layer 7 and material elements 18 can also be arranged next to one another on carrier part 6. Laterally, material elements 18 border gas-sensitive layer 7. Gas-sensitive layer 7 and material elements 18 in each case adhere directly to the surface of carrier part 6. Here as well, an adhesive agent layer can be provided between carrier part 6 and gas-sensitive layer 7 or material elements 18.

Figure 10:
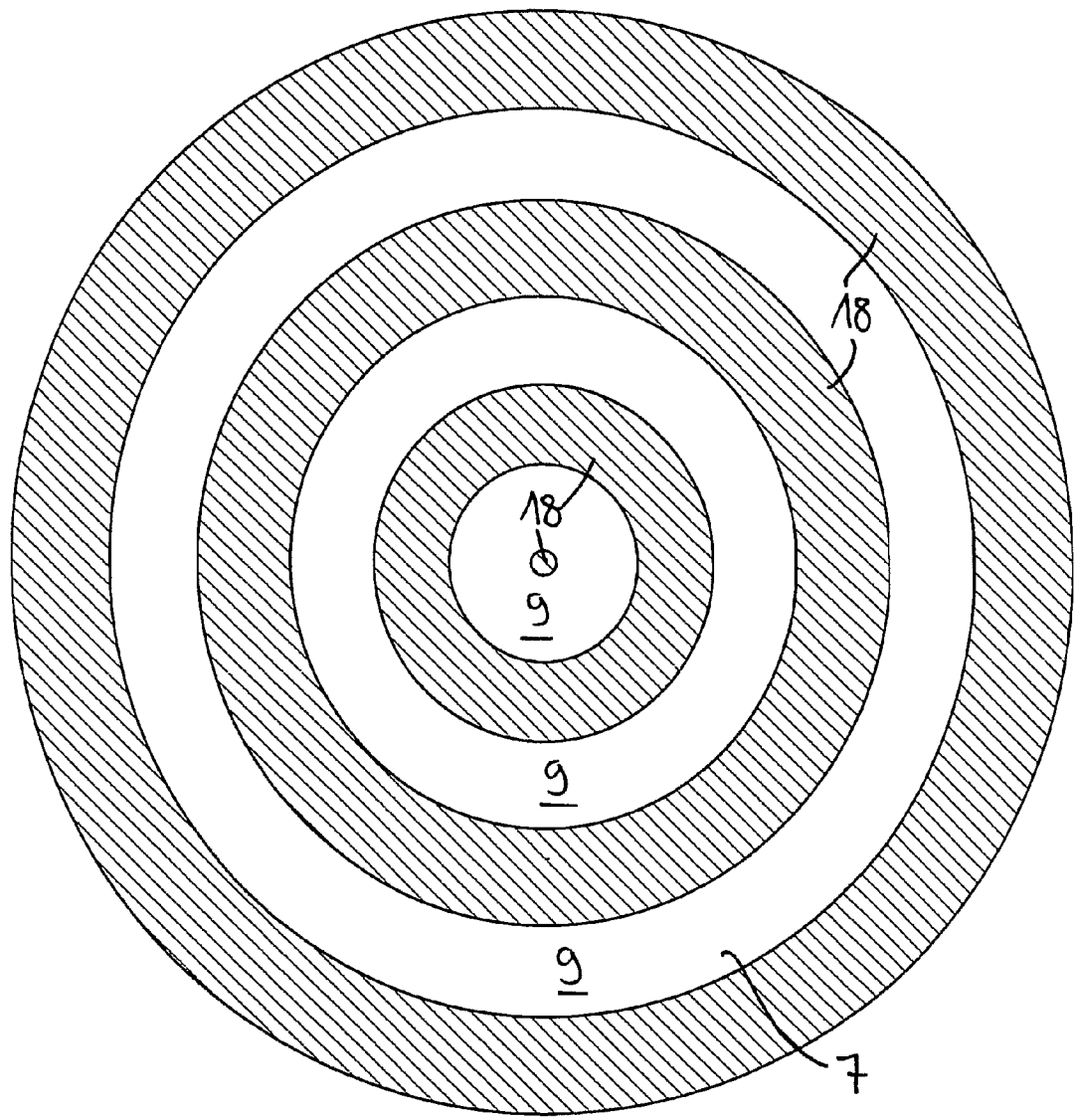
FIG. 10 shows a view of a third exemplary embodiment of a gas-sensitive layer structured by recesses.

Another exemplary embodiment is shown in FIG. 10, in which surface region 9, which can be brought into contact with the target gas, of the gas-sensitive layer has rings, between which circular material elements 18 are arranged. The rings of surface region 9 and material elements 18 in this case are arranged approximately concentric to one another. The structure shown in FIG. 10 has several conceived unit structure regions, which are embodied in the form of segments and are offset to one another in an angular grid around a center in such a way that they are adjacent to one another without interruptions.

The invention being thus described, it will be obvious that the same may be varied in many ways. Such variations are not to be regarded as a departure from the spirit and scope of the invention, and all such modifications as would be obvious to one skilled in the art are to be included within the scope of the following claims.

What is claimed is:

1. A gas sensor comprising:
at least one gas-sensitive, electrically conductive layer that has a surface region that is adapted to be brought into contact with a target gas and in which a work function is dependent on a concentration of the target gas in contact therewith; and
at least one electrical potential sensor capacitively coupled to the surface region via an air gap,
wherein the surface region is structured by recesses,
wherein the gas-sensitive layer is electrically connected with a flat material element,
wherein the material element is arranged on the gas-sensitive layer and one of the recesses or wherein one of the recesses is in the gas-sensitive layer and the material element is arranged under or in one of the recesses,
wherein a material of the material element is different than a material of the gas-sensitive layer and comprises at least one metal and/or at least one metal-containing chemical compound, and
wherein the structure formed by the surface region and the material element has at least two matching unit structure regions, which are adjacent laterally and each comprise one material element and a section of the surface region of the gas-sensitive layer.

2. The gas sensor according to claim 1, wherein the structure formed by the surface region and the material element is produced with a masking step or by photolithography.

3. The gas sensor according to claim 1, wherein the at least one metal comprises silver and/or copper.

4. The gas sensor according to claim 1, wherein the at least one metal comprises iron, tin, lead, nickel, zinc, and/or cobalt.

5. The gas sensor according to claim 1, wherein the surface region, which is brought into contact with the target gas, of the gas-sensitive layer is greater than 1%, greater than 5%, or greater than 10% of the surface, which is brought into contact with the target gas, of the at least one material element located within the at least one recess.

6. The gas sensor according to claim 1, wherein the surface, which is brought into contact with the target gas, of the at least one material element, located within the recesses, is greater than 0.001%, greater than 0.1%, or greater than 10% of the surface region, which can be brought into contact with the target gas, of the gas-sensitive layer.

7. The gas sensor according to claim 1, wherein the surface region, which is brought into contact with the target gas, is structured in such a way that the surface region is not in any place more than 500 µm, more than 300 µm, or more than 100 µm away from the material element.

8. The gas sensor according to claim 1, wherein at least two of the material elements are spaced apart laterally from one another by a subregion, located between the elements, of the gas-sensitive layer and a distance of the material elements is at least 50 nm, at least 75 nm, or at least 100 nm.

9. The gas sensor according to claim 1, wherein a thickness of the flat material elements is at least 0.1 times the thickness of a monolayer and at most 10 µm.

10. The gas sensor according to claim 1, wherein the at least one material element is arranged on the gas-sensitive layer.

11. The gas sensor according to claim 1, wherein the gas-sensitive layer is arranged on a metal layer and at least one subregion, not covered by the gas-sensitive layer, of the metal layer forms the at least one material element.

12. The gas sensor according to claim 1, wherein an adhesive agent layer is arranged between the at least one material element and the gas-sensitive layer.

13. The gas sensor according to claim 1, wherein the target gas is a reducing gas or hydrogen.

14. The gas sensor according to claim 1, wherein the sensor is a field-effect transistor, which has a substrate on which a drain and a source are arranged, a channel region is formed between the drain and the source, and the channel region is capacitively coupled to the surface region of the gas-sensitive layer directly via the air gap or indirectly via a gate electrode working together with the channel region and a sensor electrode conductively connected to the gate electrode.

15. The gas sensor according to claim 1, wherein the sensor is a Kelvin probe in which the potential sensor is capacitively coupled to the surface region of the gas-sensitive layer via an electrode separated by the air gap from the surface region of the gas-sensitive layer and movable toward and away from the gas-sensitive layer.

16. The gas sensor according to claim 1, wherein the electrically conductive layer is a metal.

17. The gas sensor according to claim 16 wherein said electrically conductive layer is one of palladium or platinum.

18. The gas sensor according to claim 1 wherein said material element does not suppress the change in the work function of the gas-sensitive layer during contact with the target gas.

19. A gas sensor comprising: at least one gas-sensitive, electrically conductive element having a first material element with a first surface having a first portion and a second portion and a plurality of second material elements formed on said first portion of said first surface wherein a work function of said electrically conductive element is a function of a concentration of a target gas exposed to said second portion of said first surface and wherein one of said first material element or said second material element is at least one of a metal or a metal-containing chemical compound and is a different material element than another one of said first or second material element; and at least one electrical potential sensor capacitively coupled to said second portion of said first surface via an air gap, wherein the electrical potential sensor further includes a field-effect transistor, which has a substrate on which a drain and a source are arranged, a channel region is formed between the drain and the source, and the channel region is capacitively coupled to the said second portion of said first surface directly via the air gap or indirectly via a gate electrode working together with the channel region and a sensor electrode conductively connected to the gate electrode.

20. The gas sensor according to claim 19, wherein the sensor further includes a Kelvin probe in which the potential sensor is capacitively coupled to the said second portion of said first surface via an electrode separated by the air gap from the said second portion of said first surface and movable toward and away from the gas-sensitive electrically conductive element.

21. The gas sensor according to claim 19, wherein the said second portion of said first surface which is brought into contact with the target gas, of the gas-sensitive layer is greater than 1%, greater than 5%, or greater than 10% of said first surface.

* * * * *